US011526986B2

(12) United States Patent
Kamon

(10) Patent No.: US 11,526,986 B2
(45) Date of Patent: Dec. 13, 2022

(54) MEDICAL IMAGE PROCESSING DEVICE, ENDOSCOPE SYSTEM, MEDICAL IMAGE PROCESSING METHOD, AND PROGRAM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 263 days.

(21) Appl. No.: 16/905,888

(22) Filed: Jun. 18, 2020

(65) Prior Publication Data
US 2020/0320702 A1    Oct. 8, 2020

Related U.S. Application Data

(63) Continuation of application No. PCT/JP2018/045953, filed on Dec. 13, 2018.

(30) Foreign Application Priority Data

Jan. 10, 2018 (JP) .............................. JP2018-002005

(51) Int. Cl.
*G06K 9/00* (2022.01)
*A61B 5/00* (2006.01)
(Continued)

(52) U.S. Cl.
CPC .......... *G06T 7/0012* (2013.01); *A61B 1/0005* (2013.01); *A61B 1/05* (2013.01);
(Continued)

(58) Field of Classification Search
CPC ..................................... G06K 9/00; A61B 5/00
(Continued)

(56) References Cited

U.S. PATENT DOCUMENTS 5,235,510 A    8/1993  Yamada et al.
8,767,057 B2 *  7/2014 Morita ................... A61B 1/041
382/128
(Continued)

FOREIGN PATENT DOCUMENTS

JP    H05012352    1/1993
JP    2003271924   9/2003
(Continued)

OTHER PUBLICATIONS

"Office Action of Japan Counterpart Application" with English translation thereof, dated Feb. 16, 2022, p. 1-p. 13.
(Continued)

*Primary Examiner* — Seyed H Azarian
(74) *Attorney, Agent, or Firm* — JCIPRNET

(57) ABSTRACT

There are provided a medical image processing device, an endoscope system, a medical image processing method, and a program which detect an optimal lesion region according to an in-vivo position of a captured image. Images at a plurality of in-vivo positions of a subject are acquired from medical equipment that sequentially captures and displays in real time the images; positional information indicating the in-vivo position of the acquired image is acquired; from among a plurality of region-of-interest detection units that detect a region of interest from an input image and correspond to the plurality of in-vivo positions, respectively, a region-of-interest detection unit corresponding to the position indicated by the positional information is selected; and the selected region-of-interest detection unit detects a region of interest from the acquired image.

11 Claims, 7 Drawing Sheets

(51) Int. Cl.
*G06T 7/00* (2017.01)
*A61B 1/00* (2006.01)
*A61B 1/05* (2006.01)
*A61B 8/00* (2006.01)

(52) U.S. Cl.
CPC ............ *A61B 8/4245* (2013.01); *A61B 8/463* (2013.01); *A61B 8/469* (2013.01); *G06T 2207/10068* (2013.01); *G06T 2207/10132* (2013.01); *G06T 2207/20084* (2013.01); *G06T 2207/30096* (2013.01)

(58) Field of Classification Search
USPC ........ 382/100, 102, 106, 128–133, 153–155, 382/162, 168, 173, 181, 199, 219, 224, 382/254, 282, 286, 291; 600/425, 339; 378/4, 21
See application file for complete search history.

(56) References Cited

U.S. PATENT DOCUMENTS

| | | | |
|---|---|---|---|
| 10,092,216 | B2 | 10/2018 | Miura |
| 2005/0203417 | A1 | 9/2005 | Okuno |
| 2007/0167715 | A1 | 7/2007 | Shigemori |
| 2011/0131528 | A1 | 6/2011 | Nakamura |
| 2011/0242301 | A1* | 10/2011 | Morita ............... A61B 1/00147 382/128 |
| 2012/0101372 | A1* | 4/2012 | Teramura ............ A61B 5/6853 600/425 |
| 2014/0194722 | A1 | 7/2014 | Lee et al. |
| 2014/0228687 | A1 | 8/2014 | Park et al. |
| 2015/0181185 | A1 | 6/2015 | Ikemoto et al. |
| 2015/0230773 | A1 | 8/2015 | Cho et al. |
| 2016/0174886 | A1 | 6/2016 | Shiraishi |
| 2017/0143310 | A1* | 5/2017 | Funakubo ............... A61B 8/465 |
| 2019/0034800 | A1 | 1/2019 | Shiratani |
| 2019/0069757 | A1 | 3/2019 | Iwaki |
| 2020/0074629 | A1* | 3/2020 | Zur .................... A61B 1/00009 |
| 2020/0090548 | A1* | 3/2020 | Kimura ................ G06T 7/0016 |

FOREIGN PATENT DOCUMENTS

| | | |
|---|---|---|
| JP | 2004113629 | 4/2004 |
| JP | 2007151809 | 6/2007 |
| JP | 2011206251 | 10/2011 |
| JP | 2011212094 | 10/2011 |
| JP | 2012249956 | 12/2012 |
| JP | 2014018333 | 2/2014 |
| JP | 2014133133 | 7/2014 |
| JP | 2014151208 | 8/2014 |
| JP | 2015085152 | 5/2015 |
| JP | 2015154918 | 8/2015 |
| JP | 2016189812 | 11/2016 |
| JP | 2017213097 | 12/2017 |
| WO | 2010113479 | 10/2010 |
| WO | 2017175282 | 10/2017 |
| WO | 2017203560 | 11/2017 |

OTHER PUBLICATIONS

"International Search Report (Form PCT/ISA/210) of PCT/JP2018/045953," dated Mar. 12, 2019, with English translation thereof, pp. 1-5.
"Written Opinion of the International Searching Authority (Form PCT/ISA/237) of PCT/JP2018/045953," dated Mar. 12, 2019, with English translation thereof, pp. 1-10.
"Office Action of Japan Counterpart Application" with English translation thereof, dated Aug. 3, 2021, p. 1-p. 8.
"Decision of Refusal of Japan Counterpart Application", dated Aug. 23, 2022, with English translation thereof, p. 1-p. 6.

\* cited by examiner

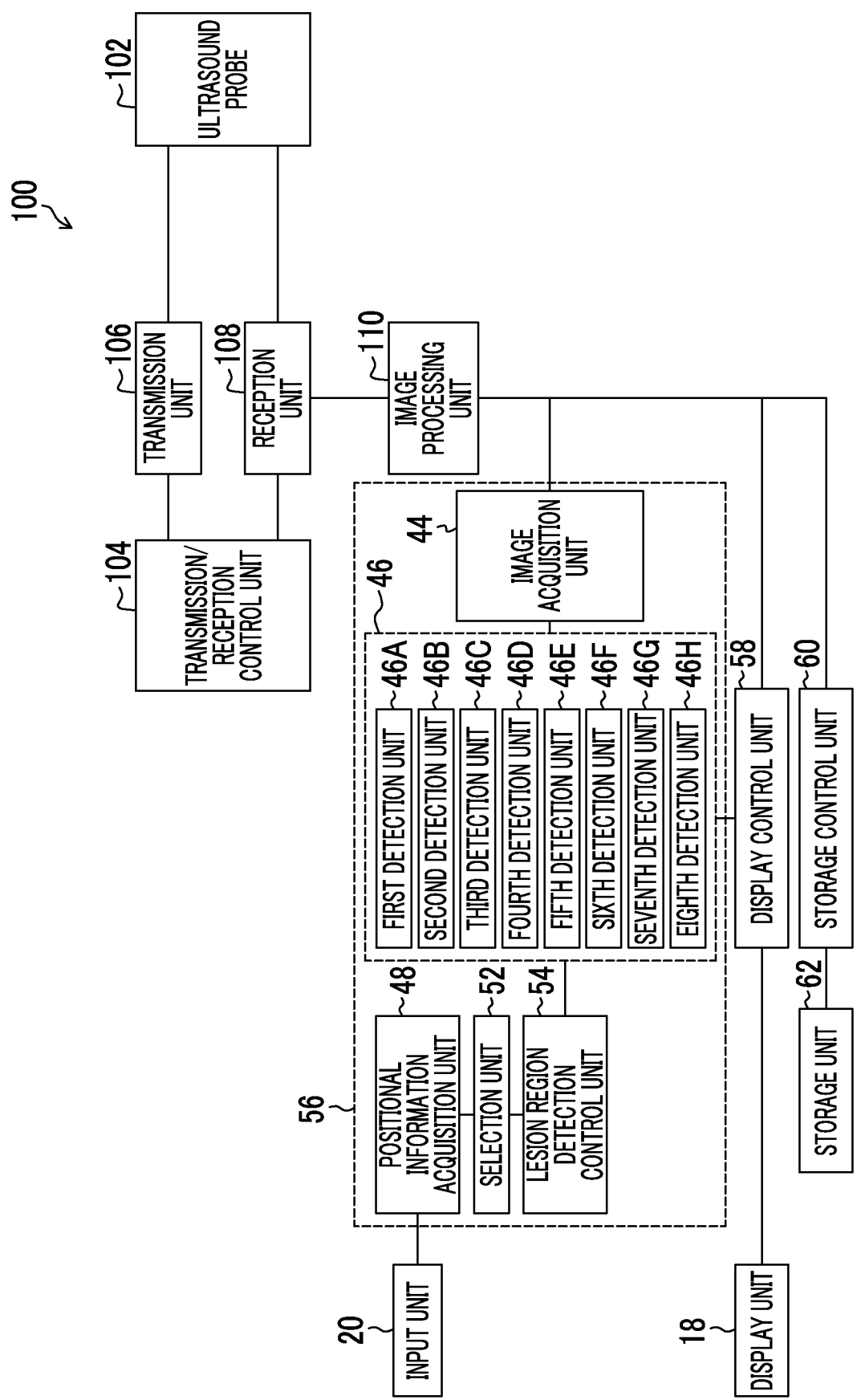

MEDICAL IMAGE PROCESSING DEVICE, ENDOSCOPE SYSTEM, MEDICAL IMAGE PROCESSING METHOD, AND PROGRAM

CROSS-REFERENCE TO RELATED APPLICATIONS

The present application is a Continuation of PCT International Application No. PCT/JP2018/045953 filed on Dec. 13, 2018 claiming priority under 35 U.S.C § 119(a) to Japanese Patent Application No. 2018-002005 filed on Jan. 10, 2018. Each of the above applications is hereby expressly incorporated by reference, in its entirety, into the present application.

BACKGROUND OF THE INVENTION

1. Field of the Invention

The present invention relates to a medical image processing device, an endoscope system, a medical image processing method, and a program, and particularly to a technique of automatically detecting a lesion region from a medical image.

2. Description of the Related Art

In a case where an endoscopic image is captured by an endoscope system, the position (part) in the lumen to be imaged is sequentially changed by the depth of an endoscope inserted into a living body. Therefore, the endoscope system performs imaging at a plurality of positions in the lumen chronologically from the start to the end of imaging.

JP2011-206251A discloses a technique of acquiring in-vivo position specifying information in a case of capturing an endoscopic image and specifying and displaying an on-model position corresponding to the in-vivo position specifying information, on a part model which is a model of a part in an object to be examined.

With the technique, it is possible to match the in-vivo position of the endoscope and the position on a guide image with high accuracy.

SUMMARY OF THE INVENTION

Image diagnosis techniques of automatically detecting a lesion region from a medical image have been known. As the automatic detection method, a detection method using the difference between a medical image and a past medical image or the difference between a medical image and a standard image, a method of detecting a lesion region by detecting the matching with a lesion pattern using pattern matching, a method of using a detector of a learned model in which the features of lesion regions accumulated in the past are learned, and the like have been known.

In the lumen imaged by the endoscope system, the structure of the mucous membrane and the characteristics of the lesion differ depending on the position thereof. Therefore, in the system of automatically detecting a lesion region from an endoscopic image, there is a problem in that it is difficult to detect an optimal lesion region depending on the imaging position of the endoscopic image. In addition to the endoscopic image, in a case where a lesion region is automatically detected from an image captured by medical equipment, which sequentially captures images at a plurality of in-vivo positions of a subject, such as an ultrasound diagnostic apparatus, there is the same problem.

The invention is made in view of such circumstances, and an object of the invention is to provide a medical image processing device, an endoscope system, a medical image processing method, and a program which detect an optimal lesion region according to an in-vivo position of a captured image.

An aspect of a medical image processing device for achieving the object is a medical image processing device comprising an image acquisition unit that acquires images at a plurality of in-vivo positions of a subject, from medical equipment that sequentially captures and displays in real time the images a positional information acquisition unit that acquires positional information indicating the in-vivo position of the acquired image; a plurality of region-of-interest detection units which detect a region of interest from an input image and correspond to the plurality of in-vivo positions, respectively; a selection unit that selects a region-of-interest detection unit corresponding to the position indicated by the positional information from among the plurality of region-of-interest detection units; and a control unit that causes the selected region-of-interest detection unit to detect a region of interest from the acquired image.

According to the aspect, the positional information indicating the in-vivo position of the image is acquired, the image being acquired from the medical equipment which sequentially captures and displays in real time the images at the plurality of in-vivo positions of the subject; from among the plurality of region-of-interest detection units that detect a region of interest from the input image and correspond to the plurality of in-vivo positions, respectively, a region-of-interest detection unit corresponding to the position indicated by the positional information is selected; and a region of interest is detected from the acquired image by the selected region-of-interest detection unit. Therefore, it is possible to detect an optimal lesion region according to the in-vivo position of the acquired image.

It is preferable that the image acquisition unit sequentially acquires a plurality of in-vivo images obtained by chronological imaging. In this manner, it is possible to detect an optimal lesion region according to the in-vivo position of the plurality of in-vivo images obtained by chronological imaging.

Further, it is preferable that the image acquisition unit sequentially acquires a plurality of images captured at a fixed frame rate. In this manner, it is possible to detect an optimal lesion region according to the in-vivo position of the plurality of images captured at a fixed frame rate.

It is preferable that the plurality of region-of-interest detection units are a plurality of learned models. In this manner, it is possible to appropriately detect a lesion region.

It is preferable that the plurality of learned models are models learned using different data sets, respectively. In this manner, it is possible to perform different detection.

It is preferable that the plurality of learned models are models learned using data sets consisting of images captured at different in-vivo positions, respectively. In this manner, it is possible to detect a lesion region according to the in-vivo position of the image.

It is preferable that the positional information acquisition unit comprises a position recognition unit that recognizes an in-vivo position from the acquired image. In this manner, it is possible to appropriately recognize the in-vivo position of the image.

Further, the positional information acquisition unit may comprise an input unit that receives the positional information through a user's input. In this manner, it is possible to appropriately recognize the in-vivo position of the image.

It is preferable that the medical image processing device further comprises a display control unit that causes the medical equipment to display the position indicated by the acquired positional information. In this manner, it is possible for the doctor to know that the position is appropriately recognized.

It is preferable that the medical equipment comprises an ultrasound probe that transmits ultrasonic waves toward an inside of the subject from an outside of the subject, and receives the ultrasonic waves reflected from the inside of the subject, an ultrasound image generation unit that generates an ultrasound image using the ultrasonic waves received by the ultrasound probe, and a display unit that displays the ultrasound image. In this manner, it is possible to detect an optimal lesion region according to the in-vivo position of the ultrasound image generated by the ultrasound diagnostic apparatus.

It is preferable that the medical equipment comprises an endoscope to be inserted into a body cavity of the subject, a camera that images the body cavity, and a display unit that displays the captured image. In this manner, it is possible to detect an optimal lesion region according to the in-vivo position of the endoscopic image generated by the endoscope system.

An aspect of an endoscope system for achieving the object is an endoscope system comprising medical equipment that has an endoscope to be inserted into a body cavity of a subject, a camera that images the body cavity, and a display unit that displays the captured image; and a medical image processing device having an image acquisition unit that acquires images at a plurality of in-vivo positions of a subject, from medical equipment that sequentially captures and displays in real time the images; a positional information acquisition unit that acquires positional information indicating the in-vivo position of the acquired image; a plurality of region-of-interest detection units which detect a region of interest from an input image and correspond to the plurality of in-vivo positions, respectively; a selection unit that selects a region-of-interest detection unit corresponding to the position indicated by the positional information from among the plurality of region-of-interest detection units; and a control unit that causes the selected region-of-interest detection unit to detect a region of interest from the acquired image.

According to the aspect, the image is acquired from the medical equipment which has an endoscope to be inserted into a body cavity of a subject, a camera that images the body cavity, and a display unit that displays the captured image and which sequentially captures the images at the plurality of in-vivo positions of the subject; the positional information indicating the in-vivo position of the image is acquired; from among the plurality of region-of-interest detection units that detect a region of interest from the input image and correspond to the plurality of in-vivo positions, respectively, a region-of-interest detection unit corresponding to the position indicated by the positional information is selected; and a region of interest is detected from the acquired image by the selected region-of-interest detection unit. Therefore, it is possible to detect an optimal lesion region according to the in-vivo position of the acquired image.

An aspect of a medical image processing method for achieving the object is a medical image processing method comprising an image acquisition step of acquiring images at a plurality of in-vivo positions of a subject, from medical equipment that sequentially captures and displays in real time the images; a positional information acquisition step of acquiring positional information indicating the in-vivo position of the acquired image; a plurality of region-of-interest detection steps of detecting a region of interest from an input image, the plurality of region-of-interest detection steps corresponding to the plurality of in-vivo positions, respectively; a selection step of selecting a region-of-interest detection step corresponding to the position indicated by the positional information from among the plurality of region-of-interest detection steps; and a control step of causing the selected region-of-interest detection step to detect a region of interest from the acquired image.

According to the aspect, the positional information indicating the in-vivo position of the image is acquired, the image being acquired from the medical equipment which sequentially captures and displays in real time the images at the plurality of in-vivo positions of the subject; from among the plurality of region-of-interest detection steps that detect a region of interest from the input image and correspond to the plurality of in-vivo positions, respectively, a region-of-interest detection step corresponding to the position indicated by the positional information is selected; and a region of interest is detected from the acquired image by the selected region-of-interest detection step. Therefore, it is possible to detect an optimal lesion region according to the in-vivo position of the acquired image.

An aspect of a program for execution of a computer for achieving the object is a program causing a computer to execute an image acquisition step of acquiring images at a plurality of in-vivo positions of a subject, from medical equipment that sequentially captures and displays in real time the images; a positional information acquisition step of acquiring positional information indicating the in-vivo position of the acquired image; a plurality of region-of-interest detection steps of detecting a region of interest from an input image, the plurality of region-of-interest detection steps corresponding to the plurality of in-vivo positions, respectively; a selection step of selecting a region-of-interest detection step corresponding to the position indicated by the positional information from among the plurality of region-of-interest detection steps; and a control step of causing the selected region-of-interest detection step to detect a region of interest from the acquired image.

According to the aspect, the positional information indicating the in-vivo position of the image is acquired, the image being acquired from the medical equipment which sequentially captures the images at the plurality of in-vivo positions of the subject; from among the plurality of region-of-interest detection steps that detect a region of interest from the input image and correspond to the plurality of in-vivo positions, respectively, a region-of-interest detection step corresponding to the position indicated by the positional information is selected; and a region of interest is detected from the acquired image by the selected region-of-interest detection step. Therefore, it is possible to detect an optimal lesion region according to the in-vivo position of the acquired image.

According to the invention, it is possible to detect an optimal lesion region according to an in-vivo position of a captured image.

BRIEF DESCRIPTION OF THE DRAWINGS

FIG. 8 is a block diagram illustrating functions of an ultrasound diagnostic apparatus.

DESCRIPTION OF THE PREFERRED EMBODIMENTS

Hereinafter, preferred embodiments of the invention will be described in detail with reference to the accompanying drawings.

First Embodiment

[Configuration of Endoscope System]

Figure 1:
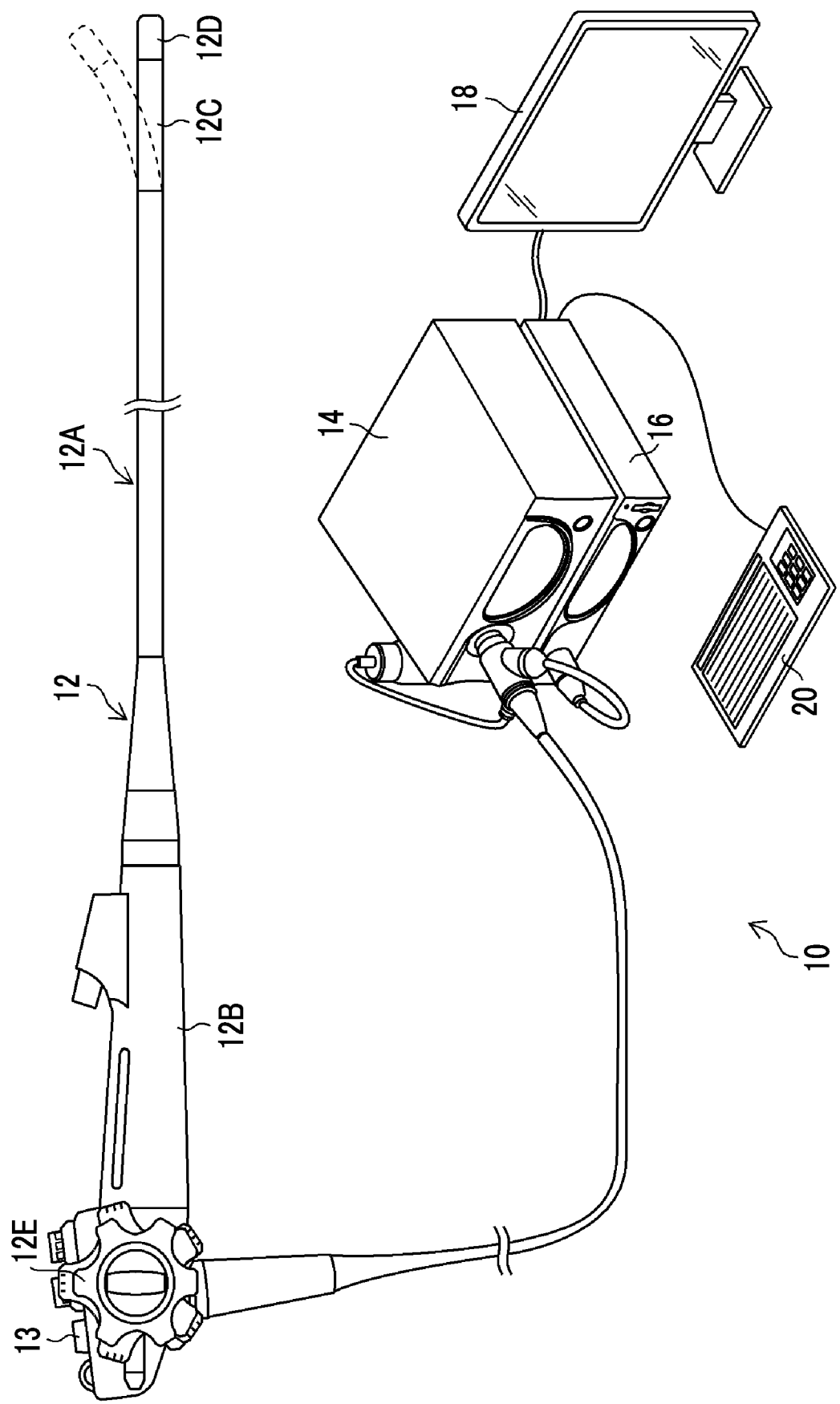
FIG. 1 is an external view illustrating an endoscope system.

FIG. 1 is an external view illustrating an endoscope system 10 (an example of medical equipment) according to a first embodiment. As illustrated in FIG. 1, the endoscope system 10 comprises an endoscope 12, a light source device 14, a processor device 16, a display unit 18, and an input unit 20.

In the embodiment, the endoscope 12 is a lower endoscope which is inserted from the anus of a subject and is used for observation of the rectum, the large intestine, and the like. The endoscope 12 is optically connected to the light source device 14. Further, the endoscope 12 is electrically connected to the processor device 16.

The endoscope 12 has an insertion part 12A that is to be inserted into a body cavity of a subject, an operation part 12B provided in a proximal end portion of the insertion part 12A, and a bendable part 12C and a distal end part 12D that are provided on the distal end side of the insertion part 12A.

An angle knob 12E and a mode switching switch 13 is provided in the operation part 12B.

The bendable part 12C is bent by operating the angle knob 12E. The distal end part 12D is directed in a desired direction by the bending operation.

The mode switching switch 13 is used in an operation of switching observation modes. The endoscope system 10 has a plurality of observation modes with different wavelength patterns of irradiation light. A doctor can set a desired observation mode by operating the mode switching switch 13. In the endoscope system 10, an image according to the set observation mode is generated by a combination of the wavelength pattern and the image processing and is displayed on the display unit 18.

Further, an acquisition instruction input unit (not illustrated) is provided to the operation part 12B. The acquisition instruction input unit is an interface for the doctor to input a static image acquisition instruction. The acquisition instruction input unit receives the static image acquisition instruction. The static image acquisition instruction received by the acquisition instruction input unit is input to the processor device 16.

The processor device 16 is electrically connected to the display unit 18 and the input unit 20. The display unit 18 is a display device that outputs and displays an image of an observation target and information associated with the image of the observation target. The input unit 20 functions as a user interface for receiving input operations such as various instructions and function setting of the endoscope system 10.

Figure 2:
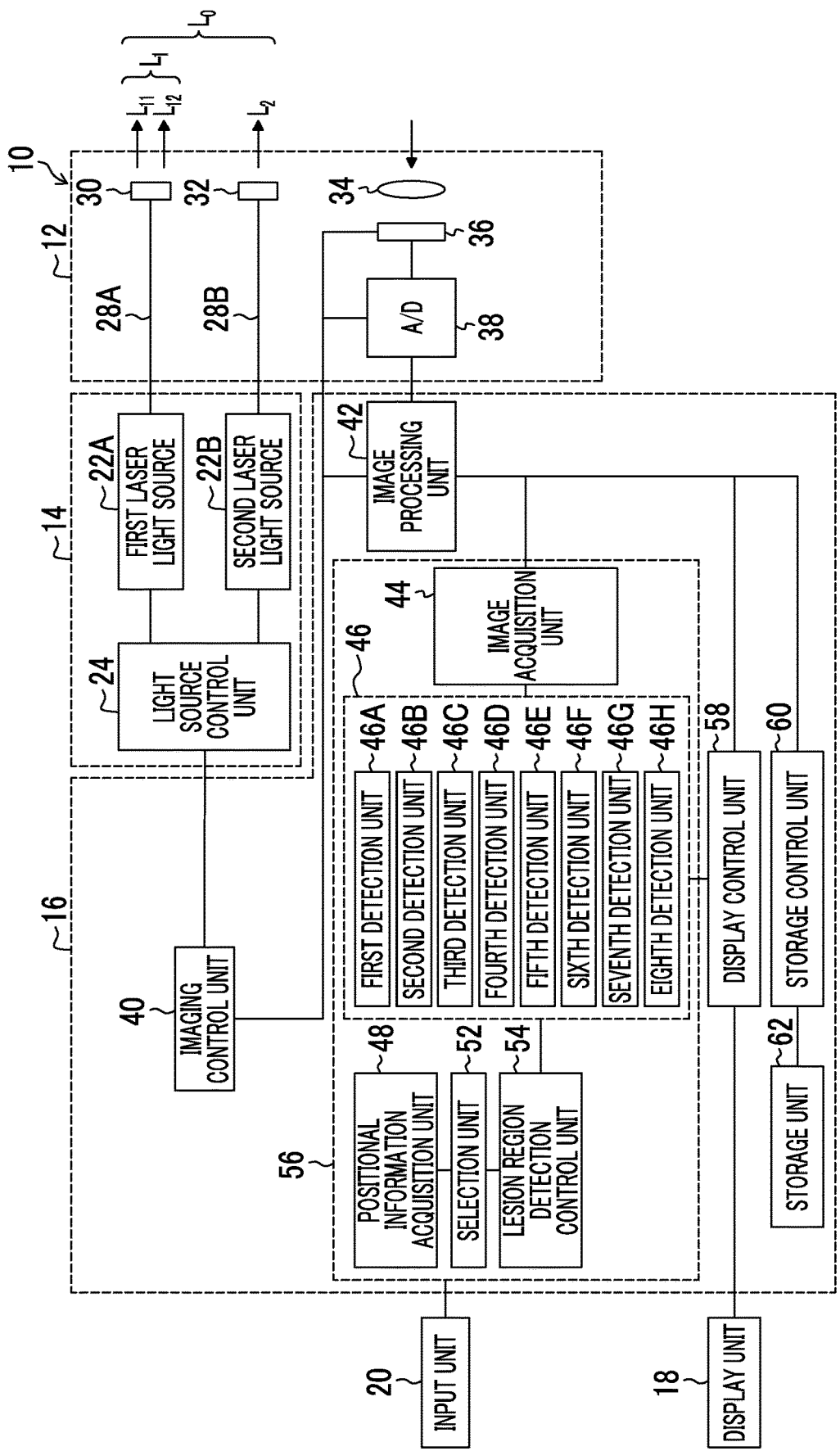
FIG. 2 is a block diagram illustrating functions of the endoscope system.

FIG. 2 is a block diagram illustrating functions of the endoscope system 10. As illustrated in FIG. 2, the light source device 14 comprises a first laser light source 22A, a second laser light source 22B, and a light source control unit 24.

The first laser light source 22A is a blue laser light source having a center wavelength of 445 nm. The second laser light source 22B is a violet laser light source having a center wavelength of 405 nm. As the first laser light source 22A and the second laser light source 22B, a laser diode can be used. Emission of the first laser light source 22A and emission of the second laser light source 22B are individually controlled by the light source control unit 24. The emission intensity ratio of the first laser light source 22A and the second laser light source 22B is freely changed.

As illustrated in FIG. 2, the endoscope 12 comprises an optical fiber 28A, an optical fiber 28B, a phosphor 30, a diffusion member 32, an imaging lens 34, an imaging element 36, and an analog-to-digital conversion unit 38.

An irradiation unit is constituted by the first laser light source 22A, the second laser light source 22B, the optical fiber 28A, the optical fiber 28B, the phosphor 30, and the diffusion member 32.

Laser light emitted from the first laser light source 22A is emitted to the phosphor 30 disposed on the distal end part 12D of the endoscope 12 by the optical fiber 28A. The phosphor 30 is configured to include a plurality of kinds of phosphors that absorb some of blue laser light from the first laser light source 22A to emit green to yellow excitation light. In this manner, light emitted from the phosphor 30 becomes white (quasi white) light $L_1$ in which green to yellow excitation light $L_{11}$ as excitation light of the blue laser light from the first laser light source 22A and blue laser light $L_{12}$ transmitted through the phosphor 30 without being absorbed to the phosphor 30 are combined.

Here, the white light is not limited to light that strictly includes all wavelength components of visible light. For example, the white light is preferably light including light in a specific wavelength range for example, R, G, and B, and broadly includes light including wavelength components from green to red, or light including wavelength components from blue to green.

On the other hand, laser light emitted from the second laser light source 22B is emitted to the diffusion member 32 disposed on the distal end part 12D of the endoscope 12 by the optical fiber 28B. As the diffusion member 32, a resin material having transmittance or the like can be used. Light emitted from the diffusion member 32 becomes light $L_2$ having a narrow-band wavelength with uniform light intensity in an irradiation region.

Figure 3:
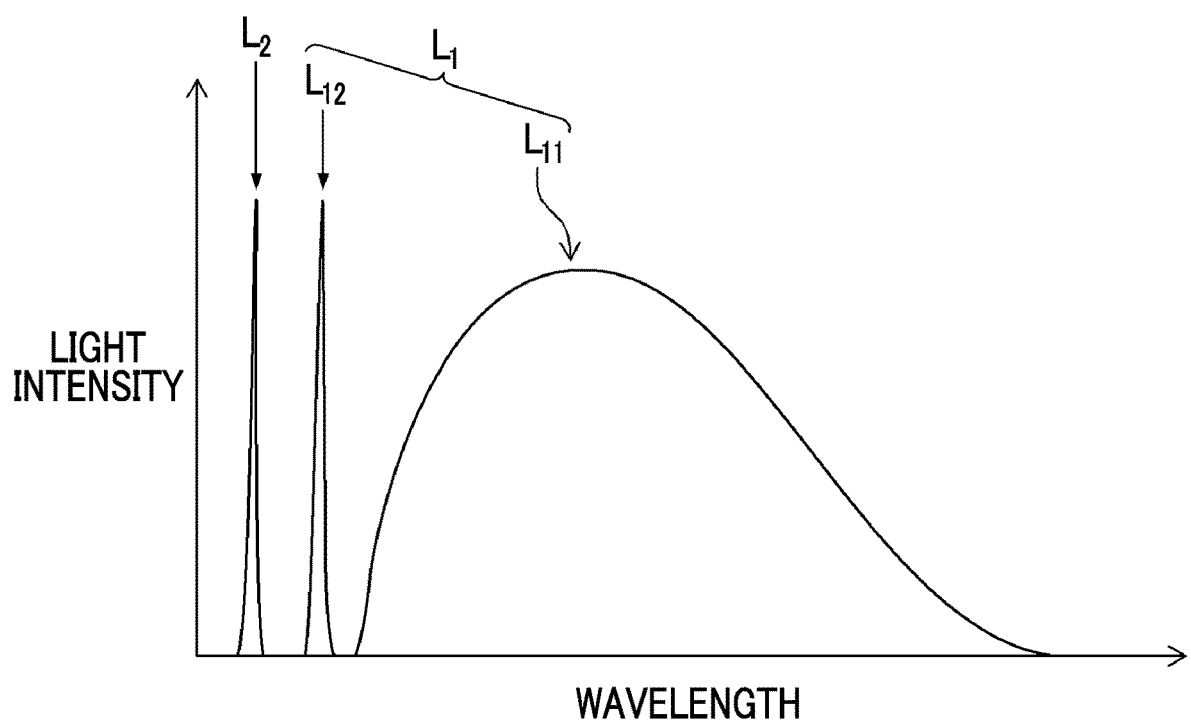
FIG. 3 is a graph illustrating an intensity distribution of light.

FIG. 3 is a graph illustrating an intensity distribution of light $L_1$ and light $L_2$. The light source control unit 24 (an example of wavelength pattern change unit) changes a light intensity ratio of the first laser light source 22A and the second laser light source 22B. In this manner, the light intensity ratio of the light $L_1$ and the light $L_2$ is changed, and the wavelength pattern of irradiation light $L_0$ as synthesis light of the light $L_1$ and the light $L_2$ is changed. Therefore, it is possible to emit irradiation light $L_0$ with the different wavelength pattern according to the observation mode.

Returning to the description of FIG. 2, an imaging unit (camera) is constituted by the imaging lens 34, the imaging element 36, and the analog-to-digital conversion unit 38. The imaging unit is disposed on the distal end part 12D of the endoscope 12.

The imaging lens 34 causes incident light to be formed on the imaging element 36. The imaging element 36 generates an analog signal according to the received light. As the imaging element 36, a charge coupled device (CCD) image sensor, or a complementary metal oxide semiconductor (CMOS) image sensor is used. The analog signal output from the imaging element 36 is converted into a digital signal by the analog-to-digital conversion unit 38, and is input to the processor device 16.

Further, as illustrated in FIG. 2, the processor device 16 comprises an imaging control unit 40, an image processing unit 42, an image acquisition unit 44, a lesion region detection unit 46, a positional information acquisition unit 48, a selection unit 52, a lesion region detection control unit 54, a display control unit 58, a storage control unit 60, and a storage unit 62.

The imaging control unit 40 generally controls imaging of a video and a static image by the endoscope system 10 by controlling the light source control unit 24 of the light source device 14, the imaging element 36 and the analog-to-digital conversion unit 38 of the endoscope 12, and the image processing unit 42 of the processor device 16.

The image processing unit 42 performs image processing on the digital signal input from the analog-to-digital conversion unit 38 of the endoscope 12 and generates image data indicating an image (hereinafter, referred to as an image). The image processing unit 42 performs image processing according to the wavelength pattern of irradiation light in a case of imaging.

The image acquisition unit 44 acquires the image generated by the image processing unit 42. That is, the image acquisition unit 44 sequentially acquires a plurality of images obtained by chronologically imaging the body cavity of a subject (an example of a living body) at a fixed frame rate. The image acquisition unit 44 may acquire an image input from the input unit 20 or an image stored in the storage unit 62. Further, an image may be acquired from an external device such as a server connected to a network (not illustrated). The images in such a case are preferably a plurality of images captured chronologically.

The lesion region detection unit 46 detects a lesion region from the input image (input image). The lesion region detection unit 46 comprises a first detection unit 46A, a second detection unit 46B, a third detection unit 46C, a fourth detection unit 46D, a fifth detection unit 46E, a sixth detection unit 46F, a seventh detection unit 46G, and an eighth detection unit 46H (an example of a plurality of region-of-interest detection units) respectively corresponding to a plurality of positions in the cavity. Here, as an example, the first detection unit 46A corresponds to the rectum, the second detection unit 46B corresponds to the sigmoid colon, the third detection unit 46C corresponds to the descending colon, the fourth detection unit 46D corresponds to the transverse colon, the fifth detection unit 46E corresponds to the ascending colon, the sixth detection unit 46F corresponds to the cecum, the seventh detection unit 46G corresponds to the ileum, and the eighth detection unit 46H corresponds to the jejunum (an example of a plurality of region-of-interest detection steps).

Each of the first detection unit 46A, the second detection unit 46B, the third detection unit 46C, the fourth detection unit 46D, the fifth detection unit 46E, the sixth detection unit 46F, the seventh detection unit 46G, and the eighth detection unit 46H is a learned model. The plurality of learned models are models learned using different data sets, respectively. Specifically, the plurality of learned models are models learned using data sets consisting of images captured at different positions in the body cavity, respectively.

That is, the first detection unit 46A is a model learned using a data set consisting of images of the rectum, the second detection unit 46B is a model learned using a data set consisting of images of the sigmoid colon, the third detection unit 46C is a model learned using a data set consisting of images of the descending colon, the fourth detection unit 46D is a model learned using a data set consisting of images of the transverse colon, the fifth detection unit 46E is a model learned using a data set consisting of images of the ascending colon, the sixth detection unit 46F is a model learned using a data set consisting of images of the cecum, the seventh detection unit 46G is a model learned using a data set consisting of images of the ileum, and the eighth detection unit 46H is a model learned using a data set consisting of images of the jejunum.

It is preferable that these learned models use a support vector machine, or a convolutional neural network.

The positional information acquisition unit 48 acquires positional information I indicating the position of the image in the body cavity, the image being acquired by the image acquisition unit 44. Here, the doctor inputs the positional information I using the input unit 20. The positional information acquisition unit 48 acquires the positional information I input from the input unit 20.

As the positional information I indicating the position of the image in the body cavity, the rectum, the sigmoid colon, the descending colon, the transverse colon, the ascending colon, the cecum, the ileum, the jejunum, and the like are input. A configuration in which these position candidates are displayed in a selectable manner on the display unit 18 and the doctor selects the position using the input unit 20 may be adopted.

The selection unit 52 selects a detection unit corresponding to the position that the positional information I acquired by the positional information acquisition unit 48 indicates, from the lesion region detection unit 46. That is, the selection unit 52 selects the first detection unit 46A in a case where the position indicated by the positional information I is the rectum, the second detection unit 46B in a case where the position indicated by the positional information I is the sigmoid colon, the third detection unit 46C in a case where the position indicated by the positional information I is the descending colon, the fourth detection unit 46D in a case where the position indicated by the positional information I is the transverse colon, the fifth detection unit 46E in a case where the position indicated by the positional information I is the ascending colon, the sixth detection unit 46F in a case where the position indicated by the positional information I is the cecum, the seventh detection unit 46G in a case where the position indicated by the positional information I is the ileum, and the eighth detection unit 46H in a case where the position indicated by the positional information I is the jejunum.

The lesion region detection control unit 54 (an example of a control unit) causes the detection unit selected by the selection unit 52 to detect a lesion region (an example of a region of interest) from the image acquired by the image acquisition unit 44. Here, the lesion region is not limited to a region caused by disease, and includes a region in a state different from a normal state in appearance. Examples of the lesion region include polyps, cancers, colonic diverticulum, inflammation, treatment scars such as endoscopic mucosal resection (EMR) scars or endoscopic submucosal dissection (ESD) scars, clip locations, bleeding points, perforations, and vascular atypia.

A medical image processing device 56 is constituted by the image acquisition unit 44, the lesion region detection unit 46, the positional information acquisition unit 48, the selection unit 52, and the lesion region detection control unit 54.

The display control unit 58 causes the display unit 18 to display an image generated by the image processing unit 42. Further, the positional information I (the position indicated by the positional information I) acquired by the positional information acquisition unit 48 is displayed. Furthermore, the lesion region detected by the lesion region detection unit 46 is superimposed and displayed on the image in a recognizable manner.

The storage control unit 60 causes the storage unit 62 to store the image generated by the image processing unit 42. For example, the image captured according to the static image acquisition instruction, and the information of the wavelength pattern of the irradiation light L0 in a case of capturing the image are stored in the storage unit 62.

The storage unit 62 is a storage device such as a hard disk. The storage unit 62 is not limited to a device built in the processor device 16. For example, the storage unit 62 may be an external storage device (not illustrated) connected to the processor device 16. The external storage device may be connected via a network (not illustrated).

The endoscope system 10 configured in this manner usually performs capturing of a video at a fixed frame rate, and causes the display unit 18 to display the captured image and the positional information I of the image. Further, a lesion region is detected from the captured video, and the detected lesion region is superimposed and displayed on the video in a recognizable manner on the display unit 18.

[Operation Method of Endoscope System]

Figure 4:
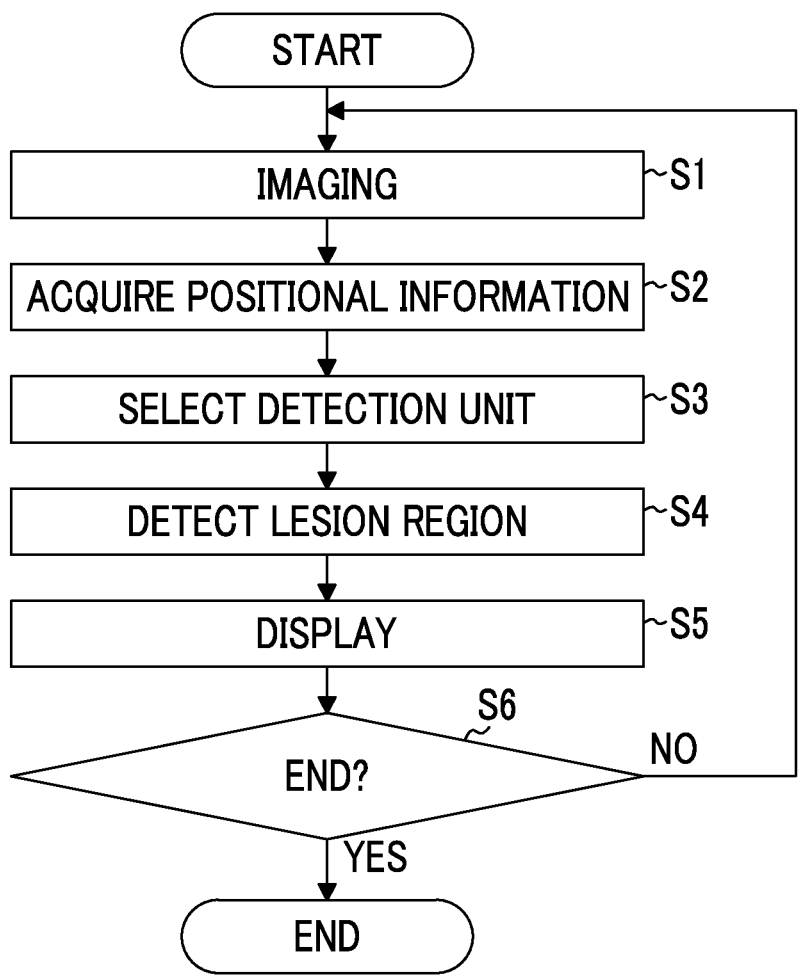
FIG. 4 is a flowchart illustrating processing of an image diagnosis method by an endoscope system 10.

FIG. 4 is a flowchart illustrating processing of an image diagnosis method by the endoscope system 10 (an example of a medical image processing method and an operation method of the endoscope system).

In starting image diagnosis by the endoscope system 10, in step S1 (an example of an image acquisition step), imaging and displaying of a video are performed under the control of the imaging control unit 40. That is, the light source control unit 24 sets light emitted from the first laser light source 22A and light emitted from the second laser light source 22B to a light intensity ratio corresponding to a desired observation mode. In this manner, irradiation light $L_0$ with a desired wavelength pattern is emitted to the part to be observed in the body cavity of the subject.

Further, the imaging control unit 40 controls the imaging element 36, the analog-to-digital conversion unit 38, and the image processing unit 42, and captures an image of the part to be observed by receiving the reflected light from the part to be observed. The image acquisition unit 44 acquires the captured image.

In this manner, the endoscope system 10 captures an image (video) at a fixed frame rate.

Next, in step S2 (an example of a positional information acquisition step), the positional information I is acquired by the positional information acquisition unit 48. Here, the doctor inputs positional information I indicating the position of the image in the lumen using the input unit 20, the image being captured in step S1. The positional information acquisition unit 48 acquires the positional information I input from the input unit 20. The doctor may input the positional information I before capturing the image.

In a case where the positional information I is newly input from the input unit 20, the positional information I, which is input last, is acquired as the current positional information I. It is sufficient that the doctor inputs the positional information I using the input unit 20 only in a case where the imaging position (part) of the endoscope 12 is changed.

Next, in step S3 (an example of a selection step), the selection unit 52 selects any detection unit among the first detection unit 46A to the eighth detection unit 46H on the basis of the positional information I acquired in step S2. That is, the first detection unit 46A is selected in a case where the position in the lumen indicated by the positional information I is the rectum, the second detection unit 46B is selected in a case where the position in the lumen indicated by the positional information I is the sigmoid colon, the third detection unit 46C is selected in a case where the position in the lumen indicated by the positional information I is the descending colon, the fourth detection unit 46D is selected in a case where the position in the lumen indicated by the positional information I is the transverse colon, the fifth detection unit 46E is selected in a case where the position in the lumen indicated by the positional information I is the ascending colon, the sixth detection unit 46F is selected in a case where the position in the lumen indicated by the positional information I is the cecum, the seventh detection unit 46G is selected in a case where the position in the lumen indicated by the positional information I is the ileum, and the eighth detection unit 46H is selected in a case where the position in the lumen indicated by the positional information I is the jejunum.

Next, in step S4 (an example of a control step), the lesion region detection control unit 54 causes the selected detection unit (an example of the selected region-of-interest detection step) to detect a lesion region from the image acquired by the image acquisition unit 44. For example, in a case where the first detection unit 46A is selected, the first detection unit 46A detects a lesion region from the image. Further, in a case where the second detection unit 46B is selected, the second detection unit 46B detects a lesion region from the image.

The first detection unit 46A to the eighth detection unit 46H have performed learning according to the positions (parts) in the lumen, respectively. Therefore, it is possible to perform appropriate detection by causing a detection unit according to the acquired positional information I to detect a lesion region.

In step S5, the display control unit 58 causes the display unit 18 to display in real time the image captured in step S1. The display in real time is processing of updating and displaying at any time the image sequentially captured, and includes the display including a time lag such as time required for the image processing and time required for communication to the display unit 18.

Further, the display control unit 58 causes the display unit 18 to display the positional information I acquired in step S3.

In a case where a lesion region is detected in step S4, the display control unit 58 causes the display unit 18 to superimpose and display the detected lesion region on the displayed image in a recognizable manner.

Figure 5:
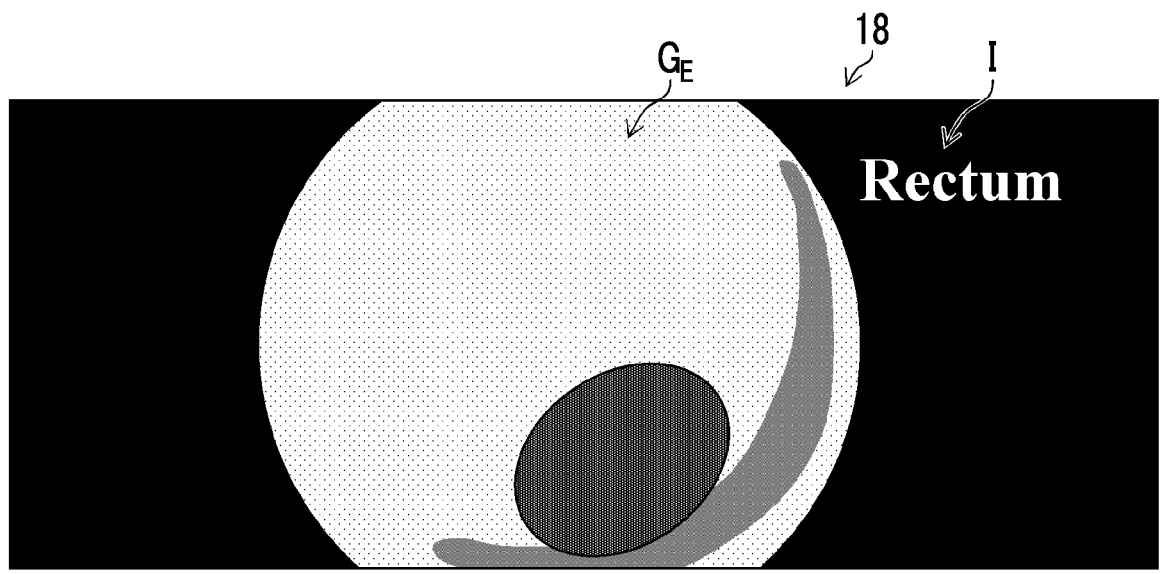
FIG. 5 is a diagram illustrating an example of a display unit in which a captured image and acquired positional information.
Figure 6:
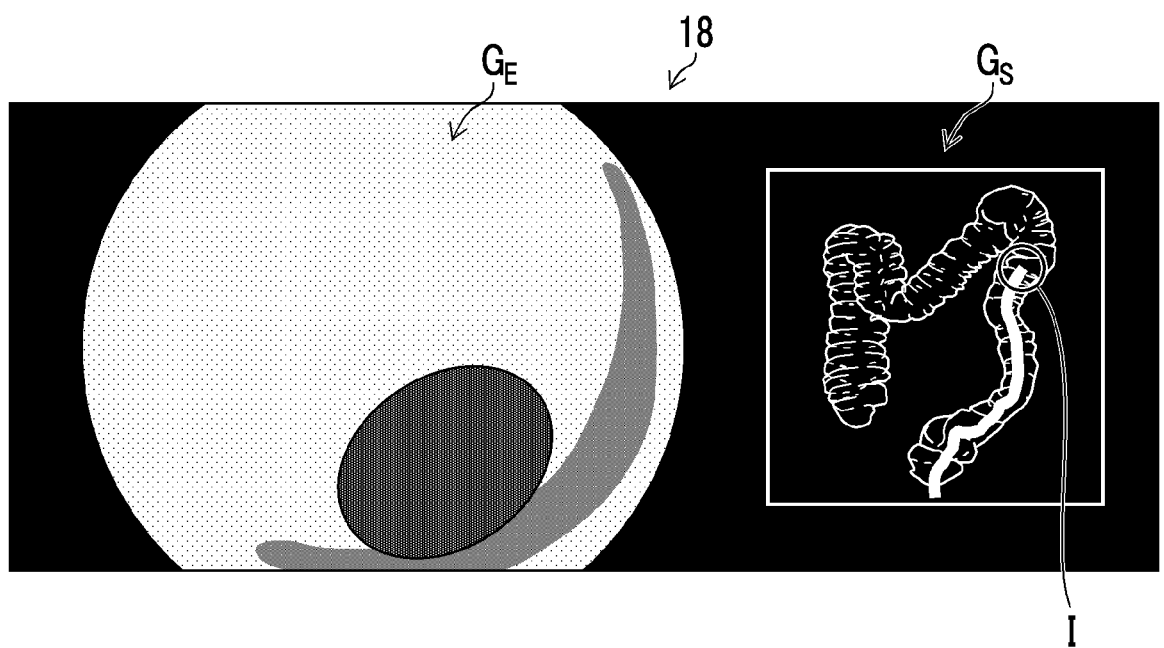
FIG. 6 is a diagram illustrating an example of a display unit in which a captured image and acquired positional information.

FIGS. 5 and 6 are diagrams illustrating an example of the display unit 18 in which a captured image GE and acquired positional information I. In the example illustrated in FIG. 5, as the positional information I, characters "Rectum" corresponding to the position indicated by the positional information I are displayed together with the image GE. Here, the positional information I is displayed in English on the upper right of the image, but the display position and the language are not limited to this example.

Further, in case illustrated in FIG. 6, as the positional information I, a schematic diagram $G_S$ of the lumen is displayed on the display unit 18 together with the image $G_E$, and a circle is displayed at the position indicated by the positional information I on the schematic diagram $G_S$. Here, a circle is used as a figure, but the shape and color are not limited thereto, and it is sufficient that the figure is displayed such that the doctor recognizes the position.

It is possible for the doctor to check that the positional information I is correctly set, by displaying the positional information I.

The storage control unit 60 causes the storage unit 62 to store the image $G_E$. Further, the image $G_E$ and the positional information I of the image $G_E$ may be associated and stored in the storage unit 62.

Finally, in step S6, it is determined whether the image diagnosis by the endoscope system 10 is to be ended. The doctor can input an end instruction of the imaging operation of the endoscope system 10, using the input unit 20.

In a case where an end instruction is input, the processing of the present flowchart is ended. In a case where an end instruction is not input, the processing returns to step S1, and imaging is continued.

In this manner, it is possible to improve the accuracy of detecting a lesion region by acquiring the positional information I and detecting the lesion region by the detection unit according to the positional information I.

Here, the endoscope system 10 acquires the positional information I by the doctor's input using the input unit 20, but the endoscope system 10 may acquire shape information of the bendable part 12C of the endoscope 12 by an endoscope insertion shape observation device (not illustrated) using a magnetic coil or the like, and may estimate the positional information I of the distal end part 12D from the shape information. Further, the subject is irradiated with X-rays from the outside to acquire the shape information of the bendable part 12C of the endoscope 12, and the positional information I of the distal end part 12D may be estimated from the shape information.

Here, an example in which the invention is applied to the lower endoscope has been described, but the invention can be applied to an upper endoscope which is inserted from the mouth or nose of the subject and is used for observation of the esophagus, stomach, and the like. In this case, as the positional information I indicating the position of the image in the body cavity, the pharynx, the esophagus, the stomach, the duodenum, and the like are input using the input unit 20. Further, the lesion region detection unit 46 may comprise detection units that detect lesion regions of the pharynx, the esophagus, the stomach, the duodenum, and the like, respectively.

Here, the lesion region detection unit 46 comprises a plurality of detection units, but the lesion region detection unit 46 may comprise one detection unit and may switch data or parameters to be used for each position. For example, the lesion region detection unit 46 comprises only the first detection unit 46A, and a parameter according to the acquired positional information I is set to the first detection unit 46A. The first detection unit 46A detects a lesion region by using the set parameter.

With such a configuration, it is possible to improve the accuracy of detecting a lesion region by detecting the lesion region by the detection unit according to the positional information I.

Second Embodiment

The positional information I is not limited to an aspect input from the outside of the endoscope system 10. For example, estimation can be performed from the captured image.

Figure 7:
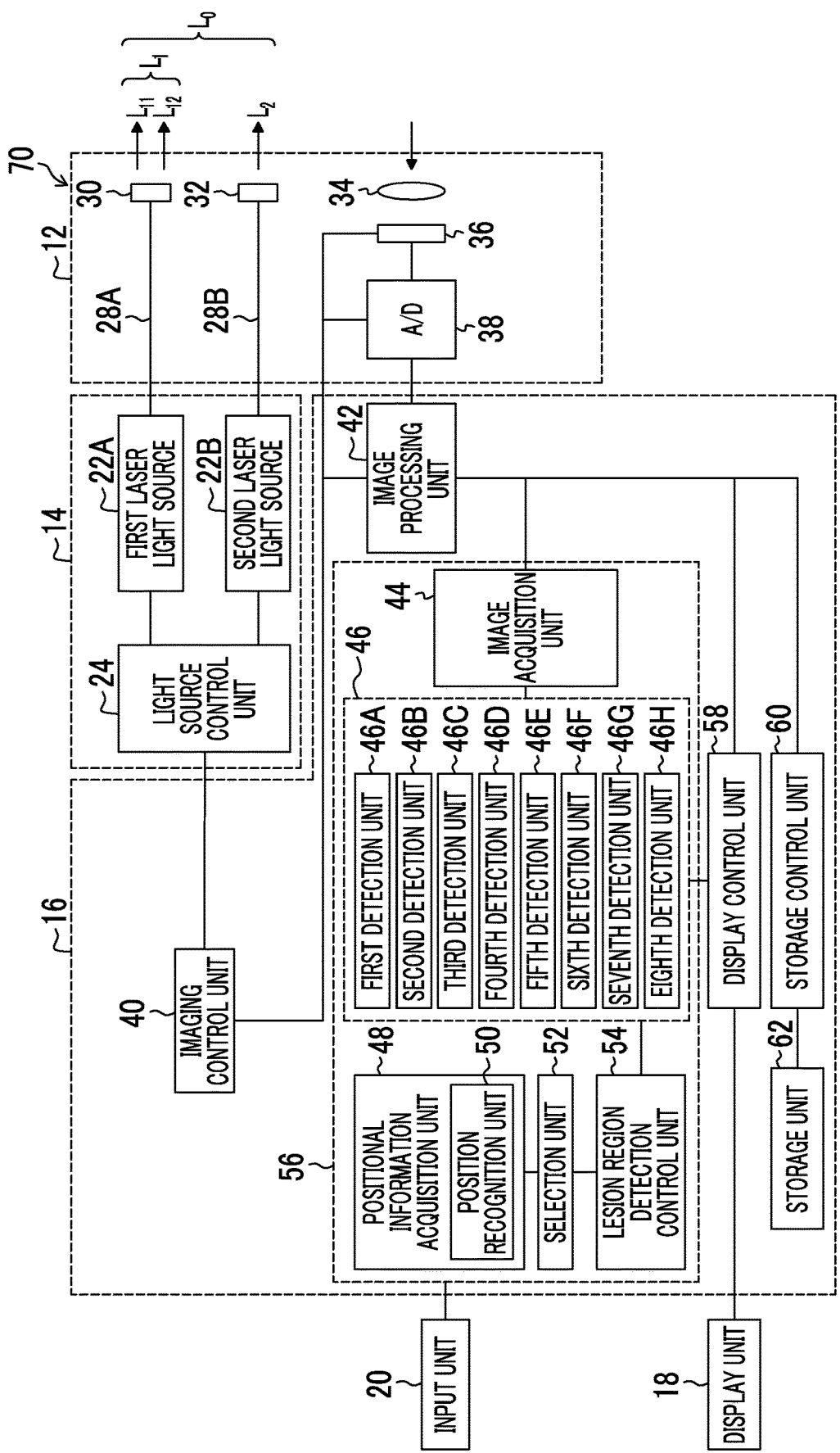
FIG. 7 is a block diagram illustrating functions of the endoscope system.

FIG. 7 is a block diagram illustrating functions of an endoscope system 70. Parts common with the block diagram illustrated in FIG. 2 are given the same reference numerals, and the detailed description thereof will be omitted.

The endoscope system 70 comprises a position recognition unit 50 in the positional information acquisition unit 48. In the embodiment, the image acquired by the image acquisition unit 44 is input to the positional information acquisition unit 48. The position recognition unit 50 recognizes (estimates) the imaged position (part) in the lumen from the image feature quantity of the input image.

For example, the position recognition unit 50 is a learned model in which images of the mucous membrane of each position are learned by a machine learning algorithm such as deep learning.

In this manner, in the endoscope system 70, it is possible to acquire the positional information I by analyzing the image in the position recognition unit 50.

The selection unit 52 selects any detection unit among the first detection unit 46A, the second detection unit 46B, the third detection unit 46C, the fourth detection unit 46D, the fifth detection unit 46E, the sixth detection unit 46F, the seventh detection unit 46G, and the eighth detection unit 46H on the basis of the acquired positional information I.

The lesion region detection control unit 54 causes the selected detection unit to detect a lesion region from the image acquired by the image acquisition unit 44.

With this configuration, it is possible to immediately acquire the positional information I in a case where the position of the distal end part 12D of the endoscope 12 is changed. In this manner, it is possible to improve the accuracy of detecting a lesion region.

Further, similar to the first embodiment, the display control unit 58 causes the display unit 18 to display the positional information I. It is possible for the doctor to check that the positional information I is correctly recognized, by displaying the positional information I. A configuration in which the positional information I can be corrected using the input unit 20 in a case where the displayed positional information I is not correct may be adopted.

The position recognition unit 50 may detect a characteristic landmark of each position, and may estimate the position from information of the detected landmark. For example, the position is estimated to be the duodenum in a case where the bile is detected as the landmark, the position is estimated to be the ileum or jejunum in a case where the villus is detected, and the position is estimated to be the cecum or ascending colon in a case where ileocecal valve is detected.

In case of the upper endoscope, in a case where the vocal cords or epiglottis is detected as the landmark, the position can be estimated to be the pharynx, and in a case where the squamous epithelium is detected, the position can be estimated to be the esophagus.

Third Embodiment

As medical equipment that sequentially captures images at a plurality of in-vivo positions of a subject, there is an ultrasound diagnostic apparatus that generates an ultrasound image. Here, an example in which the invention is applied to the ultrasound diagnostic apparatus will be described.

FIG. 8 is a block diagram illustrating functions of an ultrasound diagnostic apparatus 100. As illustrated in FIG. 8, the ultrasound diagnostic apparatus 100 comprises the display unit 18, the input unit 20, the medical image processing device 56, the display control unit 58, the storage control unit 60, the storage unit 62, an ultrasound probe 102, a transmission/reception control unit 104, a transmission unit 106, a reception unit 108, and an image processing unit 110.

In some cases, the apparatus without the ultrasound probe 102 may be referred to as the ultrasound diagnostic apparatus. In this case, the ultrasound diagnostic apparatus is connected to the ultrasound probe.

The ultrasound probe 102 transmits ultrasonic waves toward the living body from the outside of the subject, and receives the ultrasonic waves reflected from the living body of the subject.

The ultrasound probe 102 is connected to the transmission unit 106 and the reception unit 108. The transmission unit 106 and the reception unit 108 perform transmission and reception of ultrasonic waves using the ultrasound probe 102 under the control of the transmission/reception control unit 104.

The transmission unit 106 outputs a transmission signal to an ultrasonic transducer (not illustrated) that the ultrasound probe 102 comprises. The ultrasonic transducer of the ultrasound probe 102 transmits the ultrasonic waves according to the transmission signal, to the subject.

Further, the ultrasonic waves reflected from the living body of the subject are received by the ultrasonic transducer that has transmitted the ultrasonic waves. The ultrasonic transducer outputs a reflected wave signal to the reception unit 108. The reception unit 108 receives the reflected wave signal. Furthermore, the reception unit 108 performs amplification processing, analog-to-digital conversion processing, and the like on the reflected wave signal, and outputs a digital signal to the image processing unit 110.

The image processing unit 110 (an example of an ultrasound image generation unit) performs image processing on the digital signal input from the reception unit 108 to generate an ultrasound image signal.

The configurations of the display unit 18, the input unit 20, the medical image processing device 56, the display control unit 58, the storage control unit 60, and the storage unit 62 are the same as those of the endoscope system 10 according to the first embodiment.

The positional information acquisition unit 48 that the medical image processing device 56 comprises acquires the liver, the gallbladder, the pancreas, the spleen, the kidney, the uterus, the ovary, the prostate, and the like as the positional information I.

Further, in the lesion region detection unit 46 that the medical image processing device 56 comprises, the first detection unit 46A detects a lesion region of the liver, the second detection unit 46B detects a lesion region of the gallbladder, the third detection unit 46C detects a lesion region of the pancreas, the fourth detection unit 46D detects a lesion region of the spleen, the fifth detection unit 46E detects a lesion region of the kidney, the sixth detection unit 46F detects a lesion region of the uterus, the seventh detection unit 46G detects a lesion region of the ovary, and the eighth detection unit 46H detects a lesion region of the prostate.

That is, here, the first detection unit 46A is a learned model learned using a data set consisting of images of the liver, the second detection unit 46B is a learned model learned using a data set consisting of images of the gallbladder, the third detection unit 46C is a learned model learned using a data set consisting of images of the pancreas, the fourth detection unit 46D is a learned model learned using a data set consisting of images of the spleen, the fifth detection unit 46E is a learned model learned using a data set consisting of images of the kidney, the sixth detection unit 46F is a learned model learned using a data set consisting of images of the uterus, the seventh detection unit 46G is a learned model learned using a data set consisting of images of the ovary, and the eighth detection unit 46H is a learned model learned using a data set consisting of images of the prostate.

The processing of the image diagnosis method by the ultrasound diagnostic apparatus 100 is the same as the flowchart illustrated in FIG. 4.

That is, transmission and reception of ultrasonic waves are performed with respect to the subject using the ultrasound probe, and the ultrasound image signal is generated by the image processing unit 110 (step S1). This operation is performed at a fixed frame rate. Further, the positional information I regarding the position where the ultrasound image is captured is acquired by the doctor's input using the input unit 20 or the like (step S2).

The selection unit 52 selects any detection unit among the first detection unit 46A, the second detection unit 46B, the third detection unit 46C, the fourth detection unit 46D, the fifth detection unit 46E, the sixth detection unit 46F, the seventh detection unit 46G, and the eighth detection unit 46H on the basis of the positional information I (step S3). That is, the first detection unit 46A is selected in a case where the in-vivo position of the subject indicated by the positional information I is the liver, the second detection unit 46B is selected in a case where the in-vivo position of the subject indicated by the positional information I is the gallbladder, the third detection unit 46C is selected in a case where the in-vivo position of the subject indicated by the positional information I is the pancreas, the fourth detection unit 46D is selected in a case where the in-vivo position of the subject indicated by the positional information I is the spleen, the fifth detection unit 46E is selected in a case where the in-vivo position of the subject indicated by the positional information I is the kidney, the sixth detection unit 46F is selected in a case where the in-vivo position of the subject indicated by the positional information I is the uterus, the seventh detection unit 46G is selected in a case where the in-vivo position of the subject indicated by the positional information I is the ovary, and the eighth detection unit 46H is selected in a case where the in-vivo position of the subject indicated by the positional information I is the prostate.

The lesion region detection control unit 54 causes the selected detection unit to detect a lesion region from the image acquired by the image acquisition unit 44 (step S4).

The display control unit 58 causes the display unit 18 to display in real time the image captured in step S1. Further, the display unit 18 displays the positional information I (step S5). In a case where a lesion region is detected in step S4, the detected lesion region is superimposed and displayed on the image displayed on the display unit 18 in a recognizable manner.

Until it is determined in step S6 that the image diagnosis by the ultrasound diagnostic apparatus 100 is to be ended, the above operation is repeated.

As described above, also in the ultrasound diagnostic apparatus, it is possible to improve the accuracy of detecting a lesion region by acquiring the positional information I and detecting the lesion region by the detection unit according to the positional information I.

Additional Remarks

Configurations to be described below are also included in the scope of the invention in addition to the above-described aspects and examples.

(Additional Remark 1)

A medical image processing device comprising: a medical image analysis processing unit that detects a region of interest, which is a region to be noticed, on the basis of a feature quantity of pixels of a medical image; and a medical image analysis result acquisition unit that acquires an analysis result of the medical image analysis processing unit.

(Additional Remark 2)

The medical image processing device comprising: a medical image analysis processing unit that detects presence or absence of an object to be noticed, on the basis of a feature quantity of pixels of a medical image; and a medical image analysis result acquisition unit that acquires an analysis result of the medical image analysis processing unit.

(Additional Remark 3)

The medical image processing device, wherein the medical image analysis result acquisition unit acquires the analysis result of the medical image from a recording device, and the analysis result includes any one or both of the region of interest that is the region to be noticed included in the medical image and presence or absence of the object to be noticed.

(Additional Remark 4)

The medical image processing device, wherein the medical image is a normal light image that is obtained from the application of light in a white-light wavelength range or light in a plurality of wavelength ranges as the light in a white-light wavelength range.

(Additional Remark 5)

The medical image processing device, wherein the medical image is an image that is obtained from the application of light in a specific wavelength range, and the specific wavelength range is a range narrower than the white-light wavelength range.

(Additional Remark 6)

The medical image processing device, wherein the specific wavelength range is a blue-light wavelength range or a green-light wavelength range of a visible-light wavelength range.

(Additional Remark 7)

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

(Additional Remark 8)

The medical image processing device, wherein the specific wavelength range is a red-light wavelength range of a visible-light wavelength range.

(Additional Remark 9)

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

(Additional Remark 10)

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

(Additional Remark 11)

The medical image processing device, wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

(Additional Remark 12)

The medical image processing device, wherein the medical image is an in-vivo image of the inside of a living body, and the in-vivo image has information of fluorescence emitted by fluorescent materials in the living body.

(Additional Remark 13)

The medical image processing device, wherein the fluorescence is obtained from the application of excitation light, which has a peak wavelength in a range of 390 nm to 470 nm, to the inside of the living body.

(Additional Remark 14)

The medical image processing device, wherein the medical image is an in-vivo image of the inside of a living body, and the specific wavelength range is an infrared wavelength range.

(Additional Remark 15)

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

(Additional Remark 16)

The medical image processing device, wherein a medical image acquisition unit comprises a special light image acquisition unit that acquires a special light image having information about the specific wavelength range on the basis of a normal light image obtained from the application of light in a white-light wavelength range or light in a plurality of wavelength ranges as the light in a white-light wavelength range, and the medical image is the special light image.

(Additional Remark 17)

The medical image processing device, wherein a signal in the specific wavelength range is obtained by arithmetic operation based on information about colors of red, green, and blue (RGB) or cyan, magenta, and yellow (CMY) included in the normal light image.

(Additional Remark 18)

The medical image processing device further comprising: a feature-quantity-image generation unit generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, wherein the medical image is the feature quantity image.

(Additional Remark 19)

An endoscope apparatus comprising: the medical image processing device according to any one of Additional remarks 1 to 18; and an endoscope that acquires an image from the application of at least one of light in a white-light wavelength range or light in the specific wavelength range.

(Additional Remark 20)

A diagnosis support apparatus comprising: the medical image processing device according to any one of Additional remarks 1 to 18.

(Additional Remark 21)

A medical service support apparatus comprising: the medical image processing device according to any one of Additional remarks 1 to 18.

<Others>

The above-described image processing method may be configured as a program for causing a computer to realize each step, and a non-transitory recording medium such as a compact disk read-only memory (CD-ROM) in which the program is stored may be configured.

In the above-described embodiments, for example, the hardware structures of processing units executing various kinds of processing of the processor device 16 are the following various processors. The various processors include a central processing unit (CPU) as a general-purpose processor executing software (program) and functioning as various processing units, a graphics processing unit (GPU) as a processor specialized for image processing, a programmable logic device (PLD) as a processor of which the circuit configuration can be changed after manufacturing such as a field programmable gate array (FPGA), a dedicated electrical circuit as a processor having a circuit configuration designed exclusively for executing a specific process such as an application specific integrated circuit (ASIC).

One processing unit may be configured by one of the various processors, or configured by the same or different kinds of two or more processors (for example, combination of a plurality of FPGAs, combination of the CPU and the FPGA, combination of the CPU and the GPU, or the like). In addition, a plurality of processing units may be configured by one processor. As an example where a plurality of processing units are configured by one processor, first, there is an aspect where one processor is configured by a combination of one or more CPUs and software as typified by a computer, such as a server and a client, and this processor functions as a plurality of processing units. Second, there is an aspect where a processor fulfilling the functions of the entire system including a plurality of processing units by one integrated circuit (IC) chip as typified by a system on chip (SoC) or the like is used. In this manner, various processing units are configured by using one or more of the various processors as hardware structures.

Furthermore, the hardware structures of these various processors are more specifically electrical circuitry where circuit elements, such as semiconductor elements, are combined.

The technical scope of the invention is not limited to the scope described in the above embodiments. The configurations and the like in the embodiments can be appropriately combined between the embodiments in a range not departing from the gist of the invention.

Explanation of References

10: endoscope system
12: endoscope
12A: insertion part
12B: operation part
12C: bendable part
12D: distal end part
12E: angle knob
13: mode switching switch
14: light source device
16: processor device
18: display unit
20: input unit
22A: first laser light source
22B: second laser light source
24: light source control unit
28A: optical fiber
28B: optical fiber
30: phosphor
32: diffusion member
34: imaging lens
36: imaging element
38: analog-to-digital conversion unit
40: imaging control unit
42: image processing unit
44: image acquisition unit
46: lesion region detection unit
46A: first detection unit
46B: second detection unit
46C: third detection unit
46D: fourth detection unit
46E: fifth detection unit
46F: sixth detection unit
46G: seventh detection unit
46H: eighth detection unit
48: positional information acquisition unit
50: position recognition unit
52: selection unit
54: lesion region detection control unit
56: medical image processing device
58: display control unit
60: storage control unit
62: storage unit
70: endoscope system
100: ultrasound diagnostic apparatus
102: ultrasound probe
104: transmission/reception control unit
106: transmission unit
108: reception unit
110: image processing unit
$G_E$: image
$G_S$: schematic diagram
$L_0$: irradiation light
$L_1$: light
$L_{11}$: excitation light
$L_{12}$: laser light
$L_2$: light
S1 to S6: processing of image diagnosis method

What is claimed is:

1. A medical image processing device comprising:

a processor, configured to:

acquire images at a plurality of in-vivo positions of a subject, from medical equipment that sequentially captures and displays in real time the images;

acquire positional information indicating the in-vivo position of the acquired image;

detect a region of interest from an input image and correspond to the plurality of in-vivo positions, respectively;

select a region-of-interest detection unit corresponding to the position indicated by the positional information from among a plurality of region-of-interest detection units; and cause the selected region-of-interest detection unit to detect a region of interest from the acquired image, wherein the processor sequentially acquires a plurality of in-vivo images obtained by chronological imaging, wherein the processor sequentially acquires a plurality of images captured at a fixed frame rate, wherein the plurality of region-of-interest detection units are a plurality of learned models.

2. The medical image processing device according to claim 1, wherein the plurality of learned models are models learned using different data sets, respectively.

3. The medical image processing device according to claim 2, wherein the plurality of learned models are models learned using data sets consisting of images captured at different in-vivo positions, respectively.

4. The medical image processing device according to claim 1, wherein the processor comprises a position recognition unit that recognizes the in-vivo position from the acquired image.

5. The medical image processing device according to claim 1, wherein the processor comprises an input unit that receives the positional information through a user's input.

6. The medical image processing device according to claim 1, wherein the processor causes the medical equipment to display the position indicated by the acquired positional information.

7. The medical image processing device according to claim 1, wherein the medical equipment comprises
an ultrasound probe that transmits ultrasonic waves toward an inside of the subject from an outside of the subject, and receives the ultrasonic waves reflected from the inside of the subject,
an ultrasound image generation unit that generates an ultrasound image using the ultrasonic waves received by the ultrasound probe, and
a display unit that displays the ultrasound image.

8. The medical image processing device according to claim 1, wherein the medical equipment comprises
an endoscope to be inserted into a body cavity of the subject,
a camera that images the body cavity, and
a display unit that displays the captured image.

9. An endoscope system comprising:

medical equipment that has an endoscope to be inserted into a body cavity of a subject, a camera that images the body cavity, and a display unit that displays the captured image; and the medical image processing device according to claim 8.

10. A medical image processing method comprising:

an image acquisition step of acquiring images at a plurality of in-vivo positions of a subject, from medical equipment that sequentially captures and displays in real time the images;

a positional information acquisition step of acquiring positional information indicating the in-vivo position of the acquired image;

a plurality of region-of-interest detection steps of detecting a region of interest from an input image, the plurality of region-of-interest detection steps corresponding to the plurality of in-vivo positions, respectively;

a selection step of selecting a region-of-interest detection step corresponding to the position indicated by the positional information from among the plurality of region-of-interest detection steps; and a control step of causing the selected region-of-interest detection step to detect a region of interest from the acquired image, wherein the image acquisition step sequentially acquires a plurality of in-vivo images obtained by chronological imaging, wherein the image acquisition step sequentially acquires a plurality of images captured at a fixed frame rate, wherein the plurality of region-of-interest detection steps are a plurality of learned model.

11. A non-transitory computer readable recording medium causing a computer to realize:

in a case where a command stored in the recording medium is read out by the computer, an image acquisition step of acquiring images at a plurality of in-vivo positions of a subject, from medical equipment that sequentially captures and displays in real time the images;

a positional information acquisition step of acquiring positional information indicating the in-vivo position of the acquired image;

a plurality of region-of-interest detection steps of detecting a region of interest from an input image, the plurality of region-of-interest detection steps corresponding to the plurality of in-vivo positions, respectively;

a selection step of selecting a region-of-interest detection step corresponding to the position indicated by the positional information from among the plurality of region-of-interest detection steps; and a control step of causing the selected region-of-interest detection step to detect a region of interest from the acquired image, wherein the image acquisition step sequentially acquires a plurality of in-vivo images obtained by chronological imaging, wherein the image acquisition step sequentially acquires a plurality of images captured at a fixed frame rate, wherein the plurality of region-of-interest detection steps are a plurality of learned model.

* * * * *